United States Patent [19]

Van Arsdale et al.

[11] Patent Number: 5,253,513
[45] Date of Patent: Oct. 19, 1993

[54] DEVICE FOR DETERMINING VISCOELASTIC PROPERTIES OF LIQUIDS AND A METHOD FOR USE

[75] Inventors: William E. Van Arsdale, Houston; Hatim Motivala, Katy, both of Tex.

[73] Assignee: University of Houston, Houston, Tex.

[21] Appl. No.: 789,719

[22] Filed: Nov. 8, 1991

[51] Int. Cl.$^5$ .............................................. G01N 11/16
[52] U.S. Cl. ................................... 73/54.41; 73/54.02
[58] Field of Search .................... 73/60, 59, 818, 825, 73/843, 841, 824, 54.37, 54.39, 54.41, 54.02

[56] References Cited

U.S. PATENT DOCUMENTS

| | | | |
|---|---|---|---|
| 1,960,226 | 5/1934 | Schoenberg | 265/60 |
| 2,752,778 | 7/1956 | Roberts et al. | 73/60 |
| 3,803,903 | 4/1974 | Lin | 73/59 |
| 4,343,190 | 8/1982 | Danko et al. | 73/846 |
| 4,464,928 | 8/1984 | Dealy | 73/54 |
| 4,484,468 | 11/1984 | Gam et al. | 73/60 |
| 4,601,195 | 7/1986 | Garritano | 73/60 |
| 4,794,788 | 1/1989 | Masters et al. | 73/59 |
| 4,878,379 | 11/1989 | Deer | 73/60 |
| 5,016,481 | 5/1991 | Jacobsen et al. | 73/517 R |

FOREIGN PATENT DOCUMENTS 2149720 4/1973 Fed. Rep. of Germany .......... 73/60

OTHER PUBLICATIONS

E. C. Kuhn, "Hydrodynamic Pressure in a Viscous Fluid Film Between Axially Oscillating Circular Plates," Ph.D. Dissertation, School of Engineering & Mines, U. of Pittsburgh, 1963.
E. J. Dickinson et al., "The Viscoelastic Behavior of Confined Thin Films of Bitumen in Tension Compression," Trans. Soc. Rheology 13(4), 485-511, 1969.
Brochure from Metravib Instruments.
Brochure from Perkin Elmer.

Primary Examiner—Hezron E. Williams
Assistant Examiner—George M. Dombroske
Attorney, Agent, or Firm—Fulbright & Jaworski

[57] ABSTRACT

An apparatus and method for measuring the viscoelastic properties of thin liquid films. A liquid film is placed between and adjacent to two plates, and one of the two plates is oscillated in a normal direction. Computer analysis of the force of the oscillations and the displacement of the oscillations reveals rheometric properties of the liquid.

9 Claims, 2 Drawing Sheets

DEVICE FOR DETERMINING VISCOELASTIC PROPERTIES OF LIQUIDS AND A METHOD FOR USE

BACKGROUND OF THE INVENTION

The present invention relates to rheometers for analyzing the behavior of thin liquid films and more particularly to rheometers for measuring viscoelastic properties of liquids.

Viscoelastic properties are important in predicting how a liquid will behave under stress. Knowing these properties is becoming increasingly important as industry is starting to use polymer additives in liquid products.

Rheometers typically determine viscoelastic properties by shearing a liquid sample between plates. These surfaces are separated by a fixed gap. One plate moves relative to the other by sliding or rotating. The invention uses normal oscillations of a sample between parallel plates to determine viscoelastic properties. This approach accurately characterizes liquids with a wide range of viscosity. The technique is inherently simpler to implement at a significantly lower cost relative to prior art rheometers.

SUMMARY OF THE INVENTION

It is an object of the present invention to inexpensively, easily, and accurately measure the viscoelastic properties of fluids by normally oscillating a small liquid sample between two parallel, circular plates.

It is a further object of the present invention to measure $G'$ and $G''$, the storage and loss moduli of viscoelastic fluids.

To achieve the foregoing objects, there is disclosed an oscillatory squeezing flow rheometer for analyzing the behavior of thin fluid films, comprising parallel first and second plates for receiving a fluid film, an oscillatory shaker motor attached to the first plate, means for measuring force exerted by the shaker motor on the first plate, and means for measuring oscillation displacement of the first plate.

Also to achieve the foregoing objects, there is disclosed a method of determining viscoelastic properties of liquids comprising the steps of placing a liquid circularly between and in contact with parallel plates, sinusoidally oscillating one of the plates in a direction normal to the other plate, measuring the radius of the fluid circle, measuring the force of the oscillations, measuring the displacement of the moving plate, measuring the mean distance between the plates, measuring the frequency of the oscillations, and determining fluid properties base on those measurements.

DESCRIPTION OF THE PREFERRED EMBODIMENTS

Figure 1:
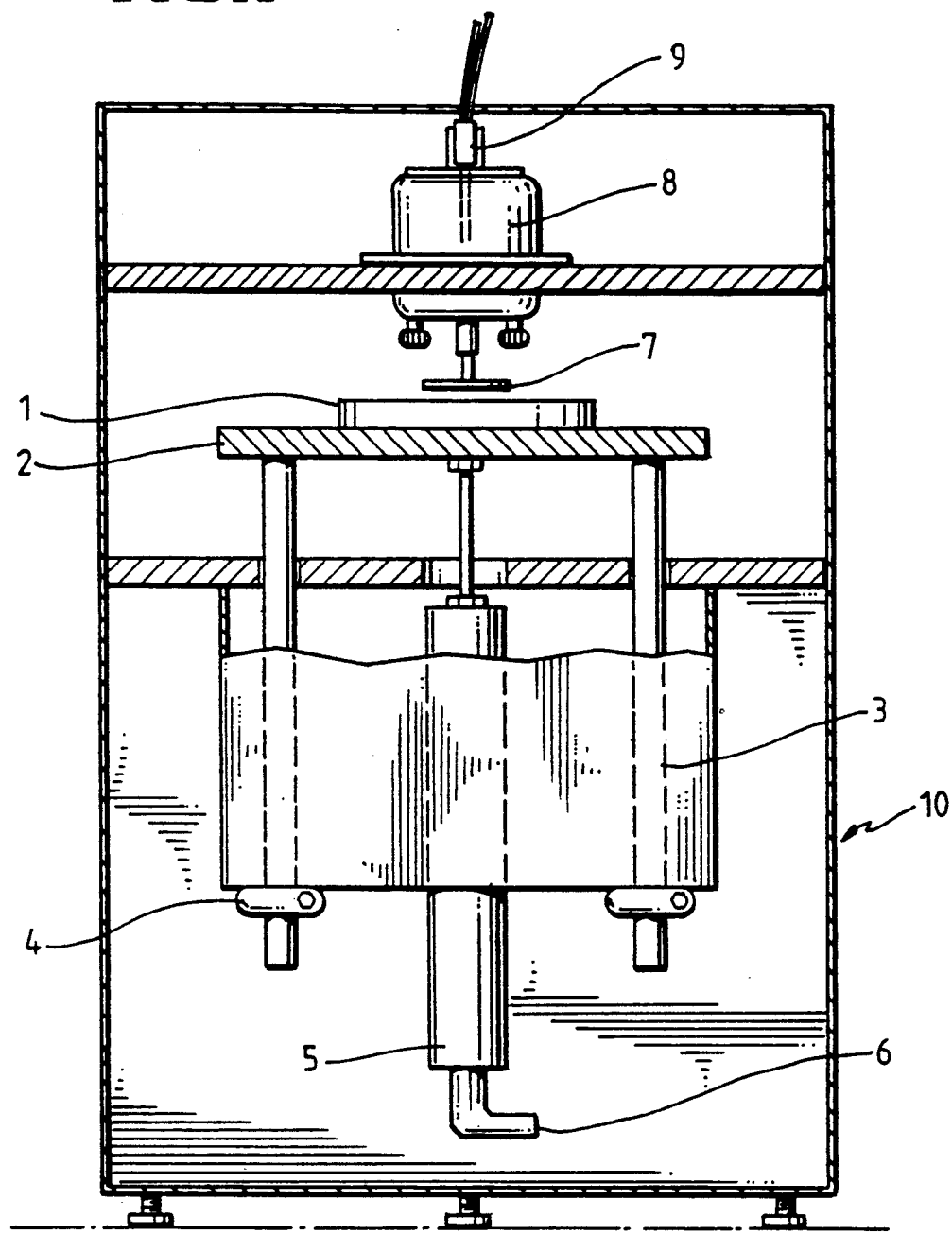
FIG. 1 is an elevational view, partly in cross-section of a typical embodiment of the invention.

Referring now to the drawings, rheometer 10 depicts a typical embodiment of the claimed invention. A temperature controlled plate 1 is mounted on a movable base plate 2. The temperature control plate 1 is desired to maintain the temperature of the liquid constant so as to stabilize the liquid's properties. The movable base plate 2 is mounted on a pneumatic linear actuator 3, having rings 4 to limit vertical movement of the base while the base is under oscillatory stress. The height of the temperature control plate 1 is controlled by pumping or releasing air through an air cylinder 5 and air supply line 6 of actuator 3. An oscillating plate 7 is connected to and extends from a shaker motor 8 such that the oscillating plate 7 is parallel to the temperature control plate 1. A displacement sensor 9 is attached to the shaker motor 8. The distance between the temperature control plate 1 and the oscillating plate 7 is controlled by adjusting a dc offset to the motor 8. A current 12 varies the force of the oscillations of the shaker motor 8, and an analog voltage signal 11 controls the current input. The sensor 9 outputs a displacement analog voltage signal 14 proportional to the displacement of the upper plate. The control plate 1 and the oscillating plate 7 are circular.

Figure 2:
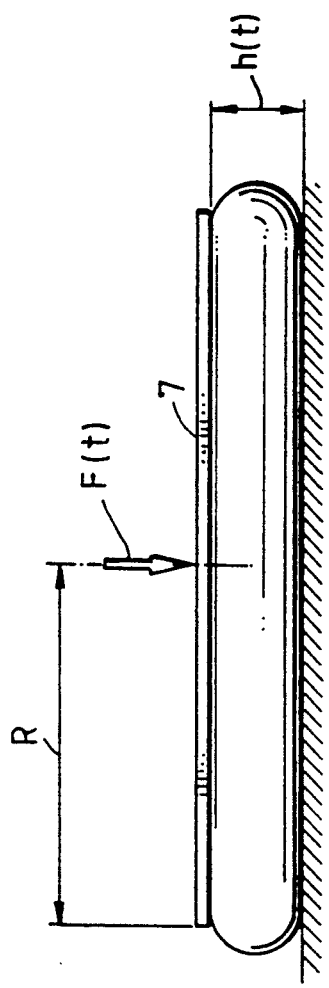
FIG. 2 depicts an enlarged cross-sectioned view of the two plates of the invention.

FIG. 2 depicts the flow geometry under consideration in the present invention. The top plate 7 is circular with radius R. This plate moves in response to a sinusoidal force with amplitude $F_0$ and frequency $\omega$ in accordance with the following formula:

$$F(t) = F_0 \sin(\omega t) \tag{1}$$

The resulting gap, in terms of the mean value $h_0$ and the imposed oscillation $x(t)$ is given by the formula:

$$h(t) = h_0 + x(t) \tag{2}$$

This motion causes a constant viscosity, or a Newtonian, fluid with viscosity $\mu$ to exert on the upper plate the force $F_n$, represented in the following formula:

$$F_n \approx -\frac{3\pi R^4 \mu \dot{x}}{2h_0^3} \tag{3}$$

A similar expression is obtained for viscoelastic fluids where $G'$ and $G''$ denote storage and loss moduli:

$$F_v \approx -\frac{3\pi R^4}{2h_0^3}\left(\frac{G''}{\omega}\dot{x} + G'x\right) \tag{4}$$

The foregoing expression assumes that the amplitude of imposed oscillations is small compared to the mean gap which is also small compared to the plate radius ($x \ll h_o \ll R$). Note that formula 3 is a special case of formula (4) in which $G' = 0$ and $\mu = G''/\omega$.

The shaker motor 8 and attached plate 7 are modeled as a second order system. The response of this system without any liquid in the gap is given by the equation:

$$\ddot{x} + 2\zeta\omega_n\dot{x} + \omega_n^2 x = \frac{F_0}{m}\sin(\omega t) \tag{5}$$

where $\omega_n$ is the natural frequency, $\zeta$ is the damping ratio, and m is the effective mass, a quantity that accounts for system inertia, such as that associated with the moving parts of the motor. The solution to the foregoing equation exhibits an amplitude ratio A, as follows:

$$A_r = \left[ \frac{\omega^4}{\omega_n^4} + \left( \frac{4\zeta^2 - 2}{\omega_n^2} \right)\omega^2 + 1 \right]^{-\frac{1}{2}} \quad (6)$$

The natural frequency and damping ratio of the system can be obtained by plotting the inverse square of the amplitude ratio ($A_r^{-2}$) versus the square of frequency ($\omega^2$) and fitting a second order polynomial through the data. It is desirable to operate the invention on either side of the natural frequency so as to minimize system response, which would mask any response associated with the sample liquid.

The presence of fluid in the gap between the two plates adds another forcing term to the equation for system response. For a viscoelastic liquid, this equation becomes:

$$\ddot{x} + \left( \frac{SG''}{m\omega} + 2\zeta\omega_n \right)\dot{x} + \left( \frac{SG'}{m} + \omega_n^2 \right)x = \frac{F_0}{m} \sin(\omega t) \quad (7)$$

in terms of the shape factor, $$S = \frac{3\pi R^4}{2h_0^2}.$$

A solution of the form $x = x_0 \sin(\omega t - \phi)$ is substituted into equation 7). This solution is expressed in terms of the oscillation amplitude $x_0$ and the phase lag $\phi$ relative to the applied force. The assumed solution is valid provided the storage and loss moduli are given the expressions:

$$G' = \frac{F_0}{Sx_0} \cos(\phi) + \frac{m}{S}(\omega^2 - \omega_n^2) \quad (8)$$

$$G'' = \frac{F_0}{Sx_0} \sin(\phi) - \frac{2m\zeta\omega\omega_n}{S} \quad (9)$$

Figure 3:
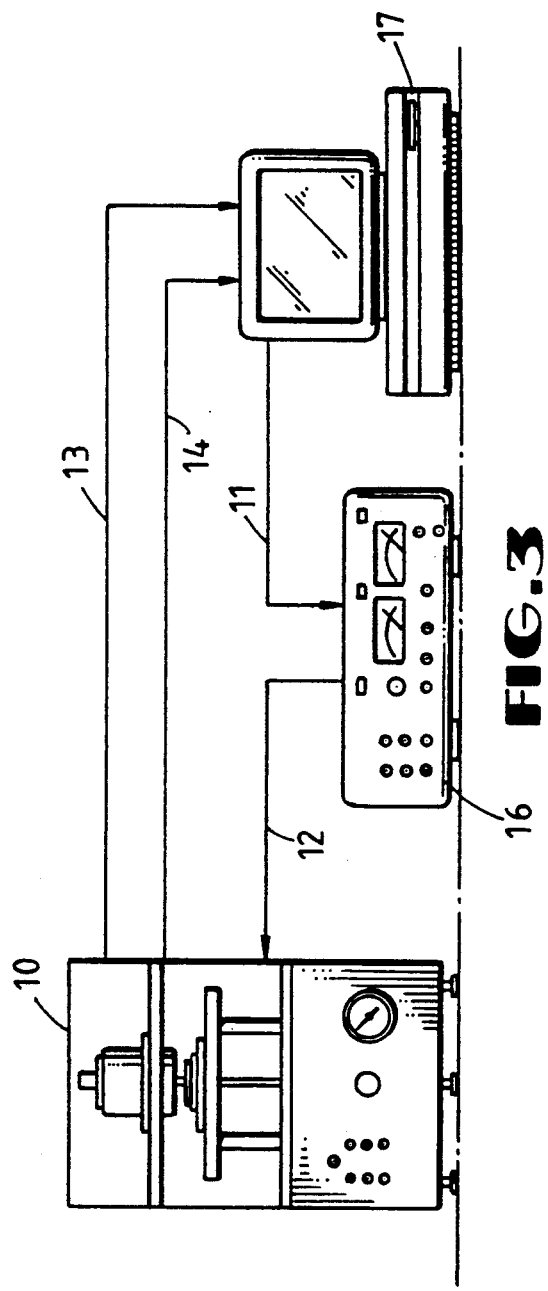
FIG. 3 is a schematic elevational view of the system using the present invention.

FIG. 3 depicts a diagram of a typical equipment array utilizing the claimed invention. The rheometer 10 sends displacement the force analog voltage signal 13 from the motor 8 and the displacement analog voltage signal 14 from the sensor 9 to a computer 17. The computer analyzes the data and calculates G' and G". The computer also supplies an analog voltage signal 11 to amplifier 16. The amplifier converts this voltage to a current 12 which is used to drive the motor 8.

The preferred oscillation means is a shaker motor comprising a moving coil assembly suspended by a magnetic field and is manufactured by Ling Dynamic Systems, Ltd. The preferred means for measuring plate displacement is a photonic sensor manufactured by Mechanical Technology, Inc., although a capacitance sensor incorporated in the motor may also be used effectively. The preferred means for measuring force exerted by the shaker motor is to monitor the voltage drop across the resistor. The force is calibrated as a function of this voltage. The preferred embodiment of the claimed rheometer includes a thermoelectric plate using components manufactured by Marlow Industries, Inc. for maintaining constant the temperature of the fluid and a linear actuator manufactured by Ultramation, Inc., for raising and lowering the lower plate to adjust the gap between the two plates. The preferred means for instrument control and data acquisition as in FIG. 3 is an Apple Macintosh II computer with hardware and software from National Instruments.

One skilled in the art will readily appreciate the present invention as well-adapted to carry out the objects mentioned as well as those inherent therein. The methods, procedures, and techniques described herein are presently representative of the preferred embodiments, are intended to be exemplary, and are not intended as limitations on the scope. Changes therein and other uses will occur to those skilled in the art which are encompassed within the spirit of the invention or defined by the scope of the claims.

We claim:

1. A method of determining viscoelastic properties of liquids comprising the steps of:
   placing a liquid circularly between and in contact with parallel plates;
   sinusoidally oscillating one of the plates in a direction normal to the other plate;
   measuring the radius of the fluid circle;
   measuring the force of the oscillations;
   measuring the displacement of the moving plate;
   measuring the mean distance between the plates;
   measuring the frequency of the oscillations; and
   determining G', the storage modulus, and G", the loss modulus, based on these measurements.

2. A method according to claim 1 having the additional step of maintaining constant the temperature of the liquid by controlling the temperature of the bottom plate.

3. A method of determining G', the storage modulus, and G", the loss modulus, of non-Newtonian fluids comprising the steps of:
   placing a liquid circularly between and in contact with parallel plates;
   measuring the radius of the fluid circle;
   measuring the means distance between the plates;
   applying a sinusoidally oscillating force to one of the plates in a direction normal to the other plate, the force oscillations having a force amplitude and a frequency;
   measuring the force amplitude;
   measuring the frequency;
   measuring the displacement amplitude of the moving plate;
   measuring a phase lag between the displacement of the moving plate and the force oscillations; and
   determining G' and G" from these measurements.

4. The method of claim 3 in which the oscillatory force is applied by a rheometer and having the additional steps of obtaining the natural frequency, the damping ratio, and effective mass of the rheometer.

5. A method according to any of claims 1, 3, or 4 in which G' and G" are determined as a function of frequency applying the measurements of the following equations:

$$G' = \frac{F_0}{Sx_0} \cos(\phi) + \frac{m}{S}(\omega^2 - \omega_n^2)$$

$$G'' = \frac{F_0}{Sx_0} \sin(\phi) - \frac{2m\zeta\omega\omega_n}{S}.$$

6. An oscillatory squeezing flow rheometer for analyzing the behavior of thin fluid films comprising:
   parallel first and second plates for receiving a fluid film;

an electric oscillatory shaker motor attached to the first plate, the motor oriented to sinusoidally oscillate the first plate normal to the second plate;

means for measuring current supplied to the shaker motor, the motor and means calibrated such that the force of the oscillations can be measured as a function of electrical current input;

means for measuring oscillation displacement at the first plate; and means for directly controlling the temperature of at least one of the two plates.

7. A rheometer according to claim 6 in which the means for measuring oscillation displacement is a photonic sensor attached to the shaker motor.

8. A rheometer according to claim 6 in which the means for measuring oscillation displacement is a capacitance sensor incorporated into the motor.

9. A rheometer according to claim 6 having a dc offset to adjust a gap between the plates.

* * * * *

UNITED STATES PATENT AND TRADEMARK OFFICE
CERTIFICATE OF CORRECTION

PATENT NO. : 5,253,513
DATED : October 19, 1993
INVENTOR(S) : Van Arsdale, et al It is certified that error appears in the above-indentified patent and that said Letters Patent is hereby corrected as shown below:

Col. 2, line 67, "A," should be -- $A_\tau$ --.

Col. 3, line 29, "φ" should be -- φ --.

Col. 3, line 30, "7)" should be -- (7) --.

Col. 3, line 31, "φ" should be -- φ --.

Col. 3, line 36, "φ" should be -- φ --.

Col. 3, line 39, "φ" should be -- φ --.

Col. 4, line 21, "fluid" should be -- liquid --.

Col. 4, line 38, "means" should be -- mean --.

UNITED STATES PATENT AND TRADEMARK OFFICE
CERTIFICATE OF CORRECTION

PATENT NO. : 5,253,513
DATED : October 19, 1993
INVENTOR(S) : Van Arsdale, et al Page 2 of 2

It is certified that error appears in the above-indentified patent and that said Letters Patent is hereby corrected as shown below:

Col. 4, line 60, "φ" should be -- φ --.

Col. 4, line 63, "φ" should be -- φ --.

Col. 4, line 63, "φ" should be -- φ --.

This certificate supersedes Certificate of Correction issued May 31, 1994.

Signed and Sealed this

Eighth Day of November, 1994

Attest:

BRUCE LEHMAN

Attesting Officer

Commissioner of Patents and Trademarks